United States Patent [19]

Takiguchi et al.

[11] Patent Number: 5,029,221
[45] Date of Patent: Jul. 2, 1991

[54] IMAGE RECONSTRUCTING APPARATUS

[75] Inventors: Yoshihiro Takiguchi; Makoto Kato, both of Shizuoka, Japan

[73] Assignee: Hamamatsu Photonics Kabushiki Kaisha, Shizuoka, Japan

[21] Appl. No.: 295,337

[22] Filed: Jan. 10, 1989

[30] Foreign Application Priority Data

Jan. 14, 1988 [JP] Japan .................................. 63-5747

[51] Int. Cl.⁵ ............................................ G06K 9/00
[52] U.S. Cl. ................................... 382/6; 364/413.13; 250/370.08
[58] Field of Search ......................... 382/6, 48, 54, 31; 250/370.08; 358/111; 364/413.13–413.16, 413.19; 378/4, 901

[56] References Cited

U.S. PATENT DOCUMENTS 4,135,247 1/1979 Gordon et al. ................. 364/413.16

Primary Examiner—Michael Razavi
Assistant Examiner—Jose L. Couso
Attorney, Agent, or Firm—Finnegan, Henderson, Farabow, Garrett, and Dunner

[57] ABSTRACT

An image reconstructing apparatus wherein the object under examination is irradiated in at least one direction to provide projection data, and the provided projection data is optically processed to form a reconstructed image representing the internal information of the object. An image associated with the projection data is formed and stored in the storage medium. The stored image is optically read out of the storage medium. The read out stored image which corresponds to one direction of irradiation is integrated at a time to produce sum data. The sum data and projection data corresponding to the same direction of irradiation are compared to form correction data. An image associated with the correction data is formed and optically superposed on the stored image in the storage medium corresponding to the same direction of irradiation, to produce the reconstructed image.

10 Claims, 5 Drawing Sheets

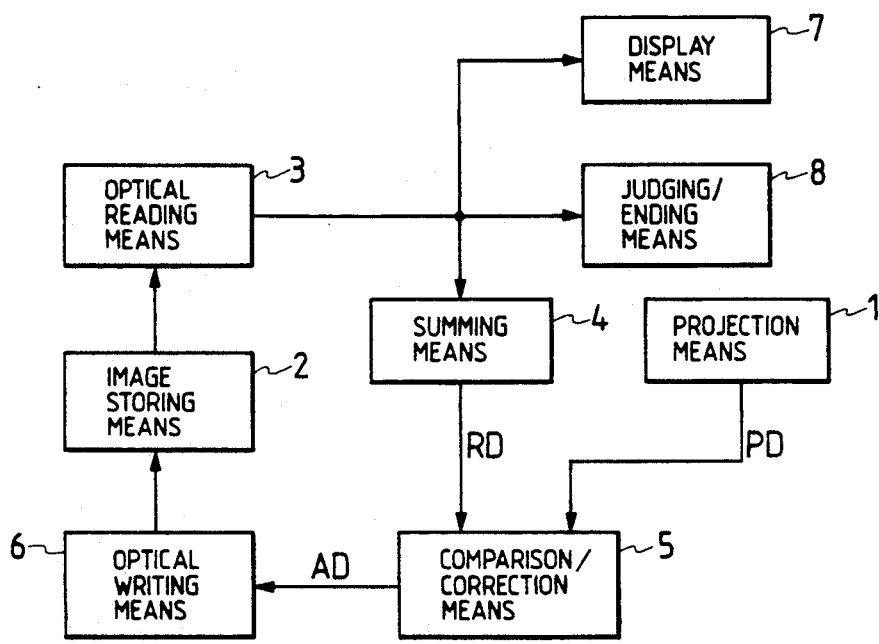
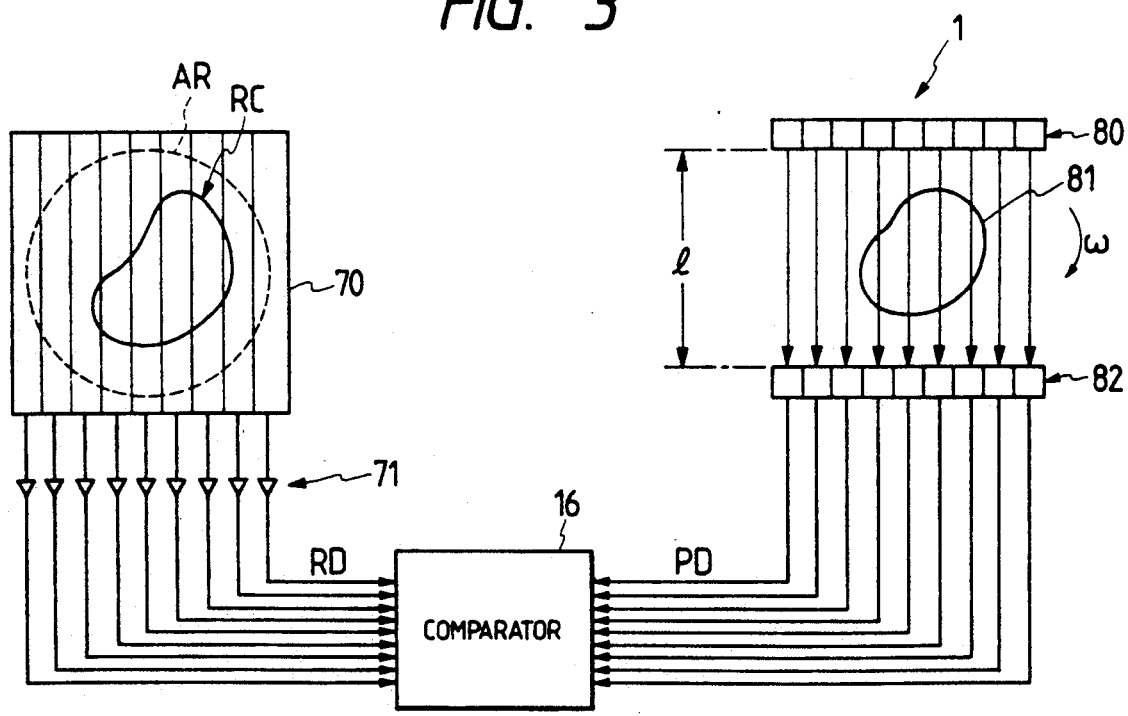

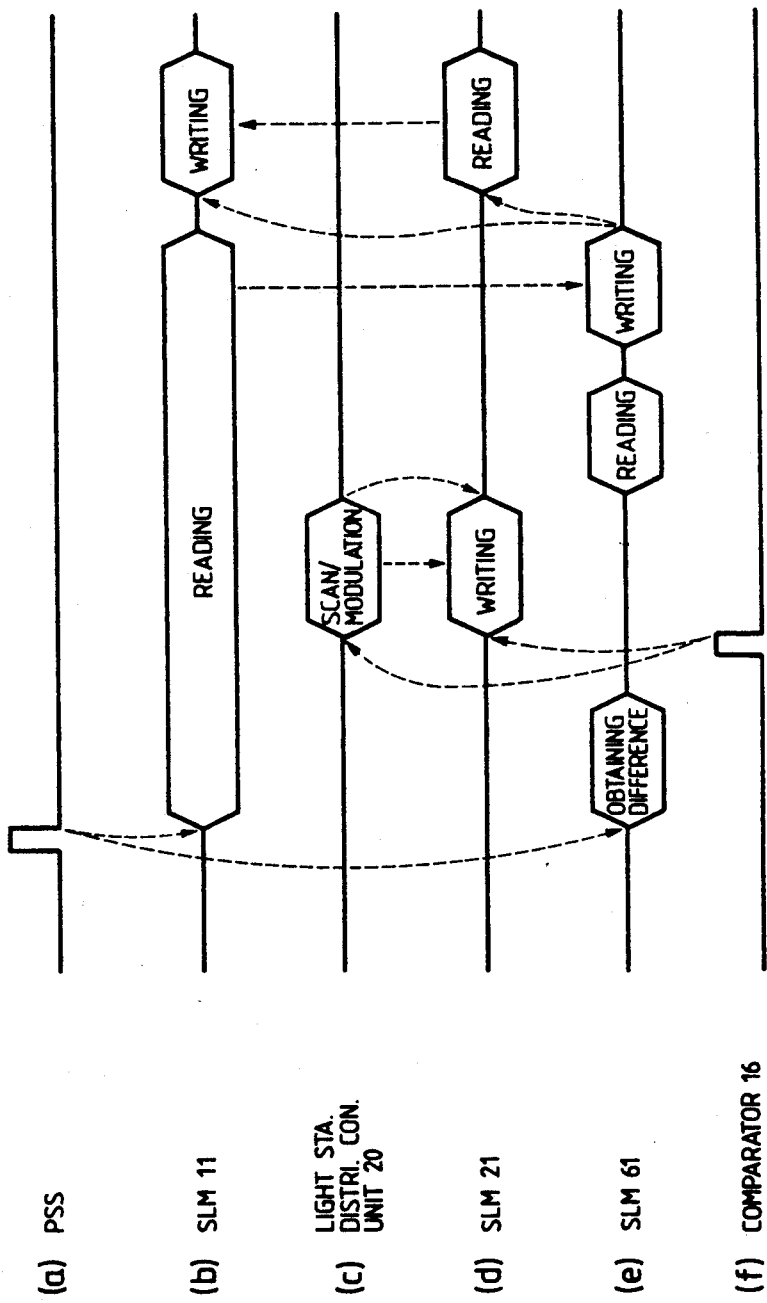

IMAGE RECONSTRUCTING APPARATUS

BACKGROUND OF THE INVENTION

This invention relates to an image reconstructing apparatus which is applied to a tomographic apparatus or the like, and more particularly relates to an image reconstructing apparatus which employs X-rays, gamma rays, neutron beams or light beams to irradiate an object under test from a plurality of directions, and obtains internal information of the object in the form of a reconstructed image on the basis of transmission data, namely, projection data in every direction.

A conventional image reconstructing apparatus is as shown in FIG. 7.

In the image reconstructing apparatus, as shown in FIG. 7, a ray source 80 applies, for instance, X-rays to an object 81 under test, and a measuring instrument 82 detects a dose of X-rays passed through the object. The dose of X-rays thus detected is a projection datum which is a result of adding internal information of the object in the direction of irradiation. The projection datum is converted into a digital value by a A/D (analog-to-digital) converter 83, which is provided to a comparator 84. In the image reconstructing apparatus, an image memory 85 is used to store a reconstructed image. The reconstructed image has picture elements the number of which corresponds to the number of internal information of the object. The data f(i,j) of the picture elements are summed in the direction corresponding to the direction of irradiation of the object 81, and provided to the comparator 84. At the beginning, the data f(i,j) of the picture elements have suitable initial values. In the comparator 84, the projection datum is compared with the sum of the data f(i,j) of the picture elements taken in the direction of irradiation, to obtain the difference value therebetween. The difference value is provided to a computer system 86. In the computer system 86, the difference values are subjected to a prescribed digital operation, to provide correction data. The correction data are superposed on the respective data f(i,j) of the elements to correct the data f(i,j) so that the difference between each internal information of the object 81 and the corresponding datum f(i,j) may be reduced.

Thereafter, either the ray source 80 or the object 81 is rotated by a predetermined angle ω, and on the basis of the projection data which are obtained with the changed direction of irradiation and the stored reconstructed image the above-described operations are carried out again. In this manner, the reconstructed image is sequentially renewed. The image processing operation is carried out until the difference between the reconstructed image and the internal information of the object becomes less than a predetermined threshold difference.

The above-described image reconstructing method, being disclosed in the literature "Iwanami Lectures, Information Science - 21, (Pattern Recognition and Figure Processing)", pp. 192 to 195, published on Mar. 10, 1983, is well known, as a iterative approximation method, in the field of image processing.

In the image reconstructing apparatus according to the conventional iterative approximation method, its image processing operations are electrically carried out; that is, the operation of comparing the projection data with the sum data of the reconstructed image, the operation of processing the difference values resulted from the comparison to obtain the correction data, and the operation of superposing the correction data on the reconstructed image to correct the latter, are digitally carried out.

However, the above-described method of digital processing is disadvantageous in the following points: The accuracy and the resolution of the reconstructed image cannot be improved without increasing the number of picture elements. Hence, each image processing operation, for instance an adding or subtracting operation takes long time. When performing the operations of rotating the reconstructed image and the correction data in response to the change of the direction of irradiation, digitally rotating the picture element matrix is considerably difficult in the points of memory capacity and processing time, thus being unsuitable for realtime processing.

SUMMARY OF THE INVENTION

Accordingly, an object of this invention is to provide an image reconstructing apparatus which can readily provide a reconstructed image high in accuracy and in resolution in a short time, and is suitable for realtime processing.

An image reconstructing apparatus according to the invention comprises: projection means in which an object under examination is irradiated with X-rays or the like, so that a projection, in the direction of irradiation, of internal data of the object is detected as projection data PD; image storing means for storing a reconstructed image; optical reading means for optically reading the reconstructed image out of the image storing means; summing means for integrating the reconstructed image thus read out in the direction corresponding to the direction of irradiation to produce sum data RD; comparison and correction means for subjecting the projection data and the sum data to comparison to form reconstructed-image-correcting data AD; and optical writing means for forming a correction function image according to the correcting data AD and optically writing the correction function image into the image storing means 2.

The image reconstructing apparatus may further comprise: display means for displaying the reconstructed image read out by the optical reading means; and judging and ending means for terminating the image reconstructing operations.

Other and further objects, features and advantages of the invention will appear more fully from the following description taken in connection with the accompanying drawings.

BRIEF DESCRIPTION OF THE DRAWINGS

FIG. 1 is a block diagram showing the arrangement of an image reconstructing apparatus according to the present invention;

FIG. 3 is an explanatory diagram showing examples of projection means and light intensity detecting unit shown in FIG. 2;

FIGS. 6(a) through 6(f) are time charts for explaining the operating procedure of the image reconstructing apparatus according to the invention.

DETAILED DESCRIPTION OF THE PREFERRED EMBODIMENTS

Figure 2:
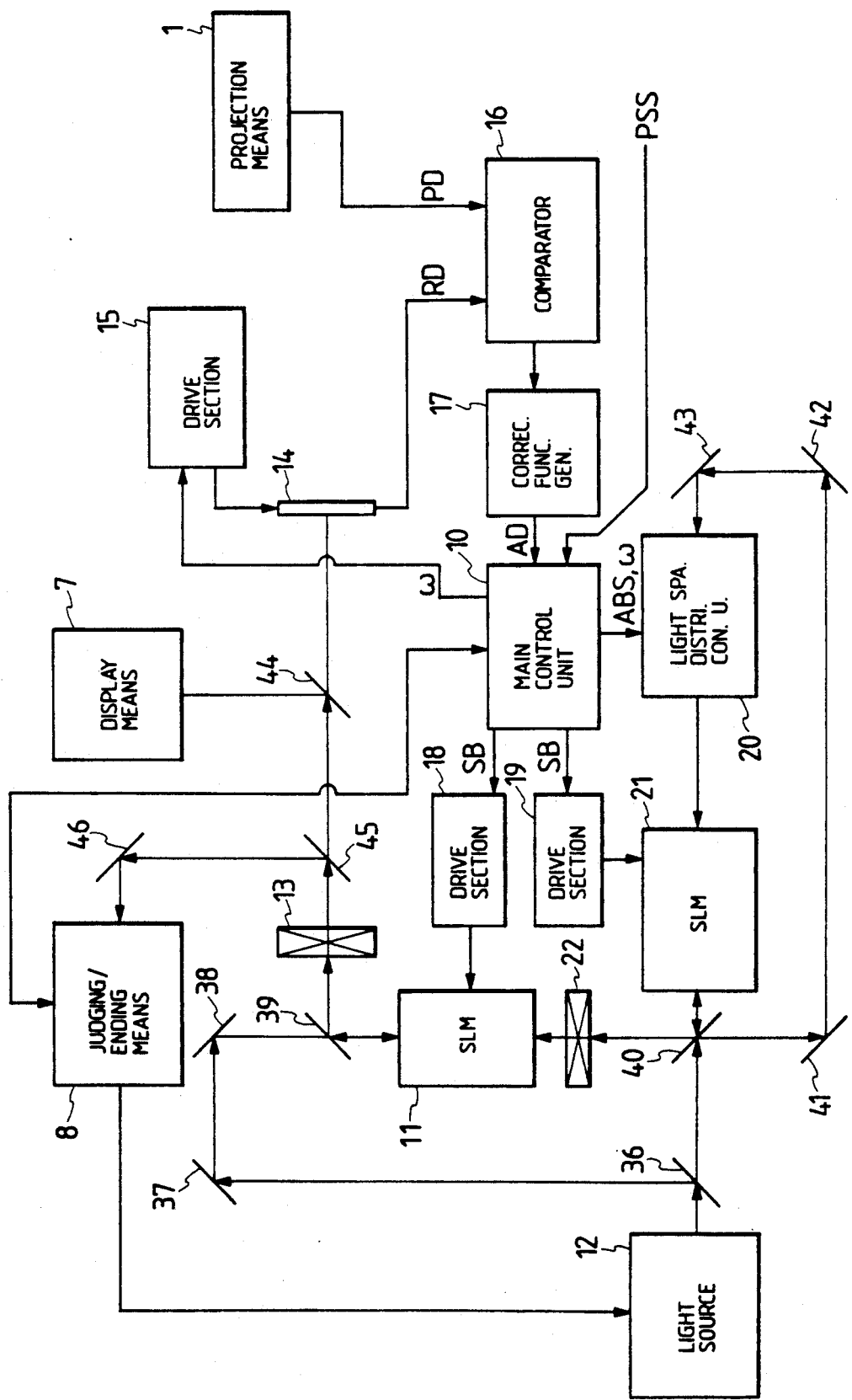
FIG. 2 is a block diagram showing the arrangement of an image reconstructing apparatus according to an embodiment of the invention.

FIG. 1 is a block diagram showing the arrangement of an image reconstructing apparatus according to the present invention.

In the image reconstructing apparatus of the invention, projection means 1 detects the projection data PD in the direction of irradiation, and summing means 4 integrates the reconstructed image which has been optically read out by optical reading means 3 in the direction corresponding to the direction of irradiation, to provide sum data RD. In a comparison and correction means 5, the projection data PD and the sum data RD in the prescribed irradiation direction are subjected to comparison, and for instance the difference therebetween is divided by the distance between a ray source and a measuring instrument for the purpose of normalization so as to be outputted as correction data AD. The correction data AD is converted into an optical correction function image.

In the conversion, the optical writing means 6 rotates the correction function image so that its direction may become in correspondence with the direction of irradiation, and optically writes the correction function image into the image storing means 2 so that it may be laid over the reconstructed image previously stored therein to correct the latter, thereby to reduce the difference between the reconstructed image and the internal information of the object under examination. Thereafter, the direction of irradiation is slightly rotated in the projection means 1, and in association with this rotating operation, the direction in which the summing means sums the reconstructed image is accordingly rotated. Under this condition, correction data AD and a correction function image are formed again, to correct the reconstructed image. In this case, the correction function image is also optically rotated as much as an angle corresponding to the rotation of irradiation by the optical writing means 6. In this manner, the direction of irradiation is gradually changed, and the reconstructed image stored in the image storing means 2 is successively optically corrected so that it may sufficiently approximate the internal information of the object under examination.

If the apparatus is provided with display means 7, then the state of the reconstructed image can be recognized. If the apparatus has a judging and ending means 8, then it can be judged whether the reconstructed image satisfactorily approximates the internal information of the object, and when the reconstructed image satisfactorily approximates the internal information of the object, the image reconstructing operations may be terminated.

One embodiment of this invention will be described with reference to the accompanying drawings.

In the embodiment, the image reconstructing operations according to the iterative approximation method as describe above is carried out in an analog mode by using optical means such as a spatial light modulator.

FIG. 2 is an explanatory diagram, partly as a block diagram, showing one example of an image reconstructing apparatus according to the invention.

As shown in FIG. 2, in the image reconstructing apparatus, a main control unit 10 controls whole image reconstructing operation; the above-described image storing means 2 in FIG. 1 comprises a spatial light modulator 11 for storing the reconstructed image; the optical reading means 3 comprises a light source 12 and an analyzer 13; the summing means 4 comprises a light intensity detecting unit 14 and a drive section 15; the comparison and correction means 5 comprises a comparator 16 and a correction function generator 17; and the optical writing means 6 comprises the main control unit 10, drive sections 18 and 19, a light spatial distribution control unit 20, a spatial light modulator 21, the light source 12, and an analyzer 22.

In the projection means 1, as shown in FIG. 3, a ray source 80 which emits X-rays, gamma rays or the like is spaced by a predetermined distance l from a measuring instrument 82, so that the dose which originates from the ray source 80 and has passed through an object 81 under examination is detected with the measuring instrument 82, and the internal information of the object 81 is projected in the direction of irradiation so as to be outputted as the projection data PD. The projection data PD have analog values and are provided to a comparator 24. The projection datum PD may be an electrical signal or optical signal.

The main control unit 10 receives a projection start signal PSS. In response to the projection start signal PSS, the main control unit 10 starts the image reconstructing operations and judges the direction of irradiation of the projection data to be inputted.

That is, in response to the projection start signal PSS, a computing operation is performed in synchronization with the inputting of the projection data PD, so that the image reconstruction is carried out in realtime.

Figure 4:
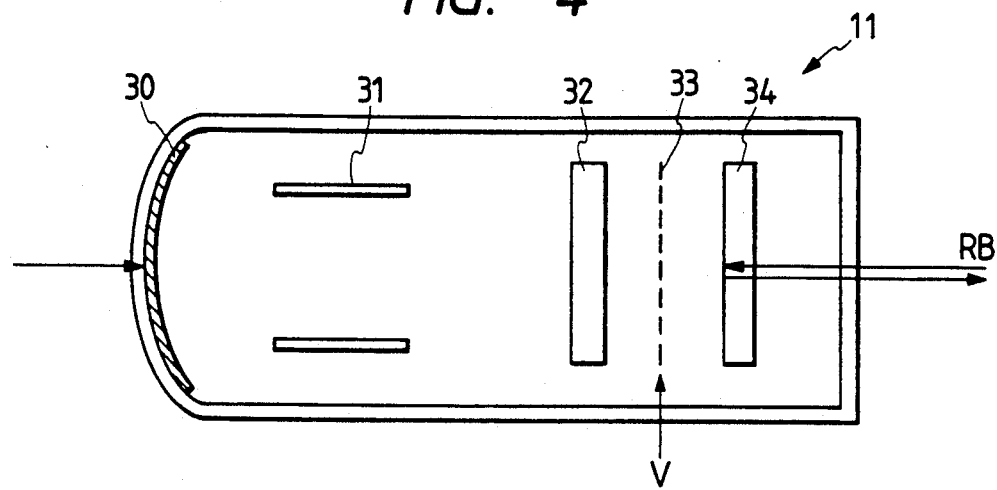
FIG. 4 is an explanatory diagram showing the structure of a spatial light modulator.
Figure 7:
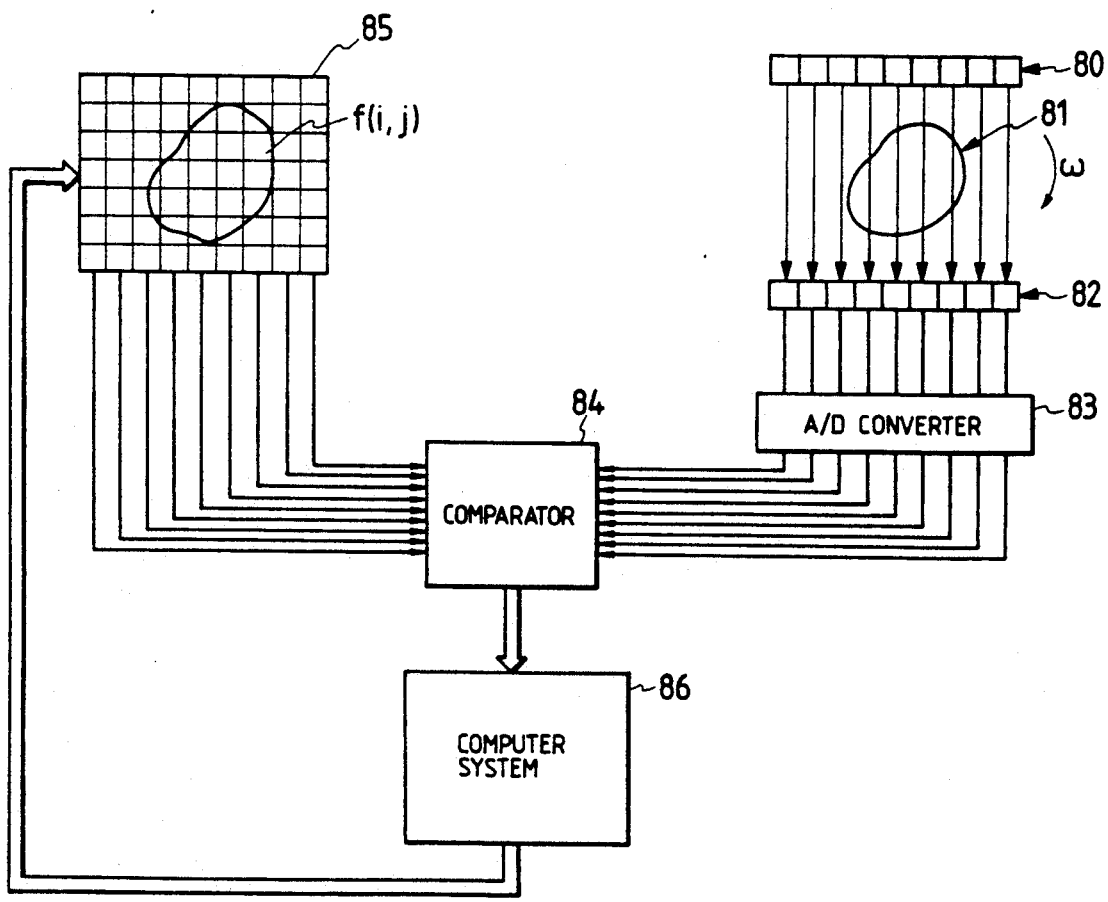
FIG. 7 is an explanatory diagram showing the arrangement of a conventional image reconstructing apparatus.

The spatial light modulator 11, as shown in FIG. 4, comprises a photocathode 30, focusing electrodes 31, a microchannel plate 32, a mesh electrode 33, and an electro-optic crystal 34, and it may be a microchannel spatial light modulator (MSLM) manufactured by Hamamatsu Photonics Kabushiki Kaisha. To the spatial light modulator 11, the correction function image provided from the spatial light modulator 21 through the analyzer 22 is provided, as a writing image WB, to the photocathode 30 thereof, where it is subjected to photoelectric conversion. A converted electron image from the photocathode 30 is provided through the focusing electrodes 31, the microchannel plate 32 and the mesh electrode 32 to the electro-optic crystal 34, where it is laid over the reconstructed image which has been already stored as an electric charge image therein, to correct the reconstructed image. At this time, depending on a potential V of the mesh electrode 32, the writing image WB and the reconstructed image stored previously are subjected to addition or subtraction in a parallel operation and in an analog mode. A refractive index distribution of the electro-optic crystal 34 is changed by the reconstructed image which is stored as the electric charge image. Therefore, when a reading light beam RB having a predetermined polarization component is made incident on the electro-optic crystal 34, a reflected reading light beam is obtained, which has experienced variation in its polarization in accordance with the refractive index distribution of the electro-optic crystal 34.

The reconstructed image is outputted in the form of light intensity distribution by extracting with the analyzer 13 a light beam having a predetermined polarization component from the reflected reading light beam RB.

The light source 12 may be a He-Ne laser which outputs a linearly polarized light beam. The linearly polarized light beam is divided into two parts by the half-mirror 36: one of the two parts is provided, as the reading light beam RB, to the spatial light modulator 11 through the mirrors 37 and 38 and the half-mirror 39, while the other is used to form the correction function image which is provided to the spatial light modulator 11.

The light intensity detecting unit 14 may comprise a movable slit and a light intensity detector (such as a photomultiplier tube) which are not shown, or may comprise, as shown in FIG. 3, an array detector (such as a silicon strip detector S2458 manufactured by Hamamatsu Photonics Kabushiki Kaisha) and an integrator. The drive section 15 comprises for instance a motor control section and a motor, and controls a rotation angle of the light intensity detecting unit 14 according to an angle datum ω which is provided from the main control unit 10 in response to the projection start signal PSS. That is, in the case where the light intensity detecting unit 14 comprises the movable slit and the light intensity detector, in order to obtain the sum of light intensities in the direction corresponding to the direction of irradiation of the projection means 1 the drive section 15 rotates the movable slit in the direction corresponding to the direction of irradiation, so that the light intensity detector detects all the output light beams from the movable slit. In the case where the array detector 70 and the integrator 70 are used in combination as shown in FIG. 3, the drive section 15 rotates the array detector 70 in the direction corresponding to the direction of irradiation, and the integrator 71 integrates the outputs, in the form of electric charge, of the array detector 70 one-dimensionally in the direction of irradiation.

The comparator 16 compares the projection data PD of the object under examination with the sum data RD of the light intensity detecting unit 14 to obtain the difference values (RD−PD) therebetween. The correction function generator 17 produces as a correction function, namely, correction data AD which are obtained by dividing the difference values (RD−PD) by the distance l between the ray source 80 and the measuring instrument 82 in the projection means 1.

The main control unit 10 divides the correction data AD into absolute value data ABS and a sign datum SB (positive or negative). After being evaluated, the sign datum SB is provided to the drive sections 18 and 19 and the absolute value data ABS are provided to the light spatial distribution control unit 20, in which sections 18 and 19 and unit 20 form the optical writing means 6. Furthermore, the main control unit 10 provides the angle datum ω of the direction of irradiation based o the projection start signal PSS not only to the drive section 15 as was described above but also to the light spatial distribution control unit 20.

Depending on the sign datum SB of the correction data AD, an instruction as to whether to perform image addition or image subtraction is provided to the drive section 18 from the main control unit 10. In response to the instruction, the drive section 18 adjusts the potential of the mesh electrode 33 so as to perform addition or subtraction of the correction function image with respect to the reconstructed image.

As was described above, the absolute value data ABS of the correction data AD, and the angular datum ω are supplied to the light spatial distribution control unit 20. The unit 20 forms a correction function image according those data, and writes it into the spatial light modulator 21. The formation of the correction function image is carried out as follows: The linearly polarized light emitted from the light source 12 is applied through the half-mirrors 36 and 40 and the mirrors 41, 42 and 43 to the light spatial distribution control unit 20, where it is modulated and made to scan the spatial light modulator 21.

The spatial light modulator 21 is similar in construction to the spatial light modulator 11, and serves as a buffer for temporarily storing the correction function image provided from the light spatial distribution control unit 20, to improve picture quality of the image. Therefore, in the case where the image may be allowed to be relatively low in picture quality, the spatial light modulator 21 may be eliminated; that is, the correction function image produced by the light spatial distribution control unit 20 may be directly applied to the spatial light modulator 11.

In FIG. 2, the display means 7 is used to display the reconstructed image sent through a half-mirror 44 from the analyzer 13. The display means 7 may be an image memory (such as an electrical memory, photographing means or hologram) which merely stores the reconstructed image, or it may be a screen, display unit or printer which actually displays a visible image. On the other hand, the reconstructed image is sent from the analyzer 13 through a half-mirror 45 and a mirror 46 to the judging and ending means 8. The means 8 judges whether or not the reconstructed image satisfactorily approximates the internal information of the object under examination, and terminates the image reconstruction operations when it is determined that the reconstructed image satisfactorily approximates the internal information of the object.

Figure 5:
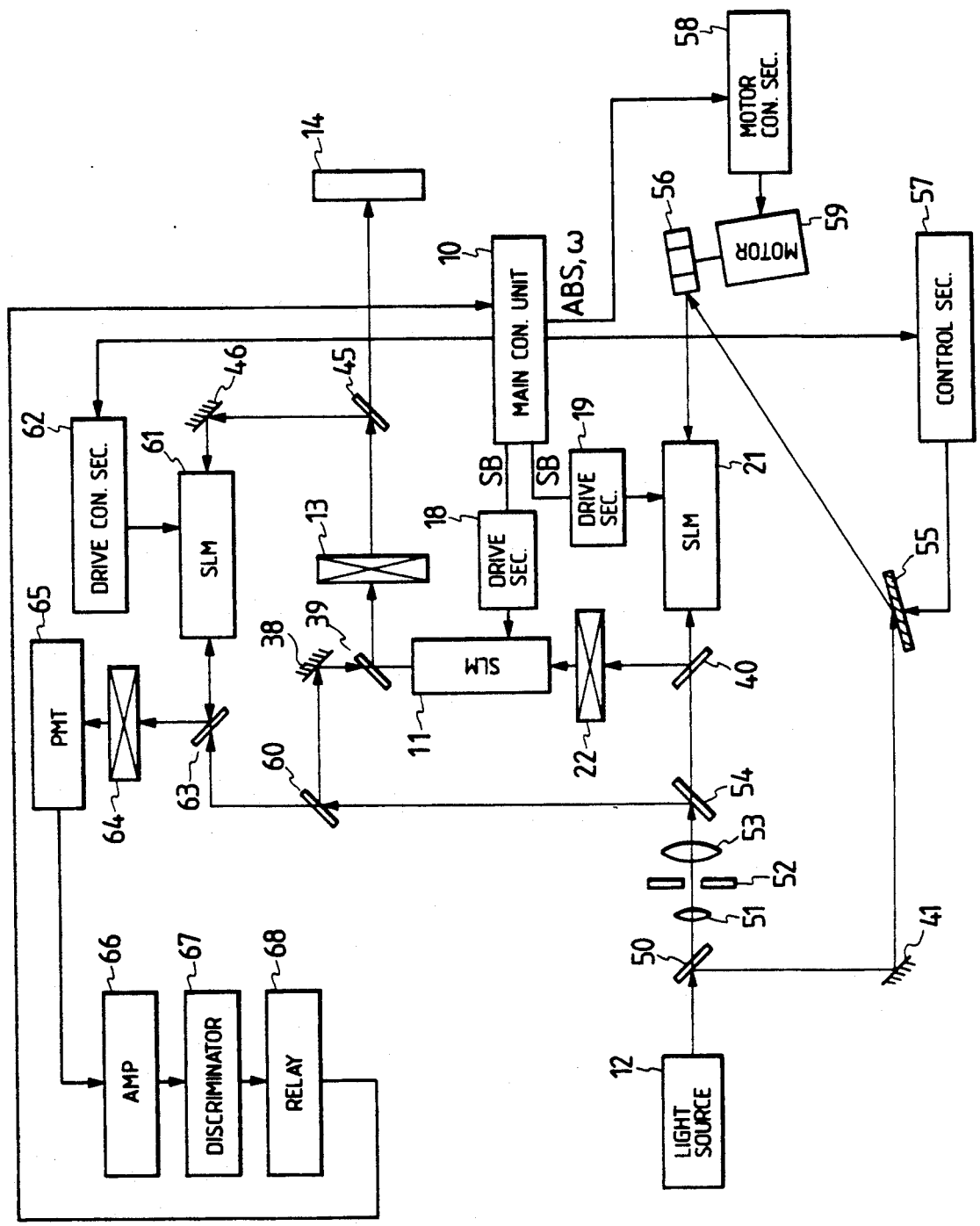
FIG. 5 is a block diagram showing the arrangement of the image reconstructing apparatus in more detail.

FIG. 5 shows the optical reading means 3, the optical writing means 6, and the judging and ending means 8 in more detail.

As shown in FIG. 5, the linearly polarized light from the light source 12 is divided into two parts by a half-mirror 50. One of the two parts is provided, as the correction function image, to the spatial light modulator 21 through mirrors 41 and 55 and a polygon mirror 56. The mirror 55 is rotated by a control section 57 according to an instruction from the main control unit 10 so as to make the linearly polarized light beam reflected from the mirror 41 scan the spatial light modulator 21. In response to instructions from the main control unit 10, a motor control section 58 controls motor 59 to control rotation speed and an angle of the polygon mirror 56. More specifically, according to the absolute value data ABS, the motor control section controls the rotation speed thereby to control the quantity of light; and according to the angular datum ω, the motor control section controls the angle thereby to control the scanning direction corresponding to the direction of irradiation. That is, the light spatial distribution control unit 20 comprising the mirror 55, the control section 57, the polygon mirror 56, the motor 59 and the motor control section 58 converts the light spatial distribution corresponding to the correction data produced by the correction function generator 17 into the correction function image which is provided to the spatial light modulator 21.

The other part of the linearly polarized light divided by the half-mirror 50 is converted into a parallel coherent light beam about 20 mm in diameter by means of lenses 51 and 53 and an aperture member 52. The parallel coherent light beam is divided into two parts by a half-mirror 54. One of the two parts is employed as a reading light beam for the spatial light modulator 21 and a writing light beam for the spatial light modulator 11, and the other is further divided into two parts by a half-mirror 60 which are employed as a reading light beam for the spatial light modulator 11 and a reading light beam for a spatial light modulator 61 (described later) in the judging and ending means 8, respectively.

The parallel coherent light beam is as large as about 20 mm in diameter. Therefore, with the parallel coherent light beam, the correction function image in a range of about 20 mm in diameter can be read out of the spatial light modulator 21 and written into the spatial light modulator 11.

The parallel coherent light beam also becomes the reading light beam for the spatial light modulator 11 as was described above. Therefore, the reading light beam is also about 20 mm in diameter, and it is made incident on the light intensity detecting unit 15 with this range. FIG. 3 shows the range AR of the reading light beam applied to the array detector 70 which is employed in the light intensity detecting unit 14, and the reconstructed image RC.

Referring back to FIG. 5, the judging and ending means 8 comprises the spatial light modulator 61, a drive control section 62, a half-mirror 63, an analyzer 64, a photomultiplier tube 65, an amplifier 66, a discriminator 67, and a relay 68.

The spatial light modulator 61 is similar in arrangement to the spatial light modulators 11 and 21. The reconstructed image from the analyzer 13 is provided through the half-mirror 45 and the mirror 46 to the spatial light modulator 61, and is stored therein. The spatial light modulator 61 compares the reconstructed image thus written-into with the reconstructed image which has been previously stored therein, to provide an image difference under the control of the drive control section 62. The image difference is read out with the reading light beam provided through the half-mirrors 60 and 63. The image difference thus read out is provided through the half-mirror 63, the analyzer 64, the photomultiplier tube 65 and the amplifier 66 to the discriminator 67, where it is judges whether it has become lower than a predetermined threshold difference. When the image difference has become lower than the threshold difference, it is determined that the reconstructed image satisfactorily approximates the internal information of the object under examination. Therefore, the relay 68 is driven to suspend the operation of the main control unit 10. Thus, the image reconstructing operations are ended.

The operations in the image reconstructing apparatus thus organized will be described with reference to time charts of FIG. 6.

First, initial conditions are given to the image reconstructing apparatus as follows: Optional initial values are written into the spatial light modulator 11 (for instance, nothing is written into), and for instance the maximum light quantity values are written into the spatial light modulator 61. When, under this condition, input of the projection data PD is started, the projection start signal PSS is generated as shown in FIG. 6(a). As a result, the reconstructed image is read out of the spatial light modulator 11 as shown in FIG. 6(b); and in the spatial light modulator 61, as shown in FIG. 6(e), the reconstructed image thus read out of the spatial light modulator 11 is compared with the reconstructed image which has been stored in the spatial optical modulator 61, to obtain the image difference.

The reconstructed image read out of the spatial light modulator 11 is supplied to the light intensity detecting unit 14. In the unit 14, a one-dimentional image in the direction corresponding to the direction of irradiation of the projecting means 1 is cut out of the reconstructed image therein, and the sum of the light intensities thereof is obtained. The sums of the light intensities are provided, as the sum data RD, to the comparator 16. The light intensity detecting unit 14 is so designed as to obtain the one-dimensional image in the direction corresponding to the direction of irradiation according to the angular datum $\omega$ provided from the main control unit 10. In the first reading operation of the spatial light modulator 11, the reconstructed image of an optional initial values preset therein is read out.

The comparator 16 operates with the timing as shown in FIG. 6(f) when both the sum data RD and the projection data PD are outputted, to subject those data to comparison thereby to obtain the difference (RD−PD) therebetween. The difference (RD−PD) is provided to the correction function generator 17, which outputs the correction data AD.

The correction data AD are provided to the main control unit 10, where it is divided into the absolute value data ABS and the positive or negative sign datum SB, which are subjected to evaluation. The sign datum SB is provided to the drive sections 18 and 19, while the data ABS is applied to the light spatial distribution control unit 20, to which the main control unit 10 supplies the angular datum $\omega$ of the direction of irradiation based on the projection start signal PSS. The light spatial distribution control unit 20 modulates the output light beam from the light source 12 and make it scan the spatial light modulator 21 according to the angular datum $\omega$ of the direction of irradiation and the absolute value data ABS of the correction data AD with the timing as shown in FIG. 6(c), to form the correction function image. The correction function image thus formed is written into the spatial light modulator 21 as shown in FIG. 6(d). In this operation, the correction function image is applied to the spatial light modulator 21 so that the corresponding parts of the correction function image and the reconstructed image may coincide with each other.

After the reconstructed image has been written into the spatial light modulator 21, the image difference is read out of the spatial light modulator 61 as shown in FIG. 6(e), and the discriminator 67 judges whether or not the image difference thus read out is lower than the predetermined threshold difference. When the image difference becomes lower than the threshold difference, it is determined that the reconstructed image satisfactorily approximates the internal information of the object under examination, and the image processing operations are ended. When the image difference is not lower than the threshold difference, the iterative approximation is carried out again. For this purpose, the reconstructed image is read out of the spatial light modulator 11 and written into the spatial light modulator 61 as shown in FIG. 6(e).

Thereafter, for the purpose of correcting the reconstructed image stored in the spatial light modulator 11, the correction function image is read out of the spatial light modulator 21 as shown in FIG. 6(d), and is written into the spatial light modulator 11 in such a manner that it is laid over the previous reconstructed image. When, in this operation, the positive (or negative) sign datum SB is provided to the spatial light modulator 11 from the drive section 18, the correction function image is written into with the writing condition of the spatial light modulator 11 switched for addition (or subtraction).

As was described above, the image adding or subtracting operation, being carried out in the spatial light modulator 11 in a parallel operation with controlling the writing condition, can be achieved in a short time. Furthermore, it is carried out in an analog mode, and therefore the reconstructed image is high both in accuracy and in resolution.

Thus, one operation cycle has been accomplished. The next operation cycle is started when the next projection start signal PSS is provided to the main control unit 10. In the next cycle, the direction of irradiation of the projection means 1 is slightly rotated and the main control unit 10 produces the angular datum ω corresponding to the rotation. According to the angular datum ω thus produced, the light spatial distribution control unit 20 in the optical writing means 6 rotates the correction function image by the angle corresponding to that of the direction of irradiation, the light intensity detecting unit 14 is rotated by the corresponding angle, and the above-described operation is carried out again.

When the direction of irradiation is rotated, the image rotating operation is optically carried out in its entirety as was described above. Therefore, even when the image has large size, the image reconstructing apparatus of the invention, being free from the problem of memory capacity, can achieve the image rotating operation quickly and very easily. Furthermore, in the image reconstructing apparatus of the invention, the image processing operation is carried out in an analog mode, and therefore the image is high both in accuracy and in resolution.

The reconstructed image is iteratively approximated in the above-described manner, to approximate the internal information of the object under examination. The reconstructed image thus processed is displayed on the display means 7 for observation of the internal information of the object.

In the above-described embodiment, the difference value (RD−PD) produced by the comparator 16 is divided by the distance l to output the correction data AD; however, the division may be performed with the difference values (RD−PD) weighted as required.

As was described above, in the image reconstructing apparatus of the invention, the image reconstructing operations including the image adding or subtracting operation and the image rotating operation is optically carried out in an analog mode, with the result that the reconstructed image high both in accuracy and in resolution can be readily and quickly obtained by realtime processing.

What is claimed is:

1. An image reconstructing apparatus comprising:
  means for exposing an object to radiation in at least one direction of irradiation;
  projection means, coupled to the exposing means, for providing projection data representing the internal information of an exposed object under examination; and
  optical processing means for optically processing the projection data for from a reconstructed image representing the internal information of the exposed object, including:
  means, coupled to the projection means, for forming an image associated with the projection data,
  image storing means, coupled to the image forming means, for storing a formed image,
  means, coupled to the image storing means, for optically reading out a stored formed image,
  means, coupled to the reading means, for integrating a read out stored image corresponding to one direction of irradiation, at a time to produce sum data,
  means, coupled to the integrating means and projecting means, for comparing the projection data and sum data each corresponding to the same direction of irradiation, to produce correction data, and
  writing means, coupled to the comparing means, for forming a correction image associated with the correction data and for optically superposing said correction image with the stored formed image in the image storing means each corresponding to the same direction of irradiation, to form the reconstructed image.

2. The image reconstructing apparatus of claim 1, further comprising means for successively changing the direction of irradiation at a predetermined angle, to provide a plurality of successive directions of irradiation, wherein
  said reading means includes means, coupled to said changing means, for reading out the stored image in accordance with a changed direction of irradiation; and
  said writing means includes means, coupled to said changing means, for forming the correction image in accordance with a changed direction of irradiation.

3. The image reconstructing apparatus of claim 1, wherein
  said exposing means includes a ray source for irradiating said object, and
  said projection means includes means for detecting rays irradiated through said object under examination, to provide the projection data.

4. The image reconstructing apparatus of claim 1, wherein
  said image storing means includes a microchannel spatial light modulator having electro-optic material for storing said formed image as an electric charge image on said electro-optic material.

5. The image reconstructing apparatus of claim 1, wherein said integrating means includes:
  a light intensity detecting means for integrating said read out stored image;
  means for turning the light intensity detecting means; and
  means for controlling said turning means for turning the light intensity detecting means.

6. The image reconstructing apparatus of claim 1, wherein said writing means includes:
  a light source for emitting a light beam;
  means for storing an image representing the correction data;
  means, coupled to the correction data image storing means, for reading out a stored image; and means, coupled to said light source and correction data image reading means, for modulating an emitted light beam with a read out stored correction data image, and for scanning said correction data image storing means with a modulated emitted light beam, to form the correction image.

7. The image reconstructing apparatus of claim 6, wherein said correction data image storing means includes a microchannel spatial light modulator for temporarily storing said correction image.

8. The image reconstructing apparatus of claim 1, further comprising means for displaying said reconstructed image.

9. The image reconstructing apparatus of claim 1, further comprising means for determining whether said reconstructed image is substantially equal to said internal information of the object under examination, and for terminating the operation of said image reconstructing apparatus in accordance with the determination.

10. The image reconstructing apparatus of claim 4, wherein
said reading means includes means for projecting a light beam onto said electro-optic material of the microchannel spatial light modulator of the image storing means and for detecting a light beam reflected therefrom.

* * * * *

UNITED STATES PATENT AND TRADEMARK OFFICE
CERTIFICATE OF CORRECTION

PATENT NO. : 5,029,221
DATED : July 02, 1991
INVENTOR(S) : Yoshihiro Takiguchi et al.

It is certified that error appears in the above-identified patent and that said Letters Patent is hereby corrected as shown below:

Claim 1, column 10, line 4, change "for" to --to--.

Claim 1, column 10, line 4, change "from" to --form--.

Claim 1, column 10, line 17 and 18 change "projecting" --projection--.

Signed and Sealed this

Twenty-third Day of March, 1993

Attest:

STEPHEN G. KUNIN

Attesting Officer

Acting Commissioner of Patents and Trademarks